(12) United States Patent
Folan

(10) Patent No.: US 11,471,311 B2
(45) Date of Patent: Oct. 18, 2022

(54) STENT DELIVERY SYSTEM WITH REDUCED DEPLOYMENT FORCE

(71) Applicant: BOSTON SCIENTIFIC SCIMED, INC., Maple Grove, MN (US)

(72) Inventor: Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 271 days.

(21) Appl. No.: 16/378,511

(22) Filed: Apr. 8, 2019

(65) Prior Publication Data
US 2019/0307591 A1    Oct. 10, 2019

Related U.S. Application Data

(60) Provisional application No. 62/654,984, filed on Apr. 9, 2018.

(51) Int. Cl.
*A61F 2/97* (2013.01)
*A61F 2/966* (2013.01)
*A61M 25/00* (2006.01)

(52) U.S. Cl.
CPC ............. *A61F 2/97* (2013.01); *A61F 2/966* (2013.01); *A61F 2002/9665* (2013.01); *A61F 2210/0014* (2013.01); *A61F 2230/0091* (2013.01); *A61M 25/0074* (2013.01)

(58) Field of Classification Search
CPC .... A61F 2/97; A61F 2/966; A61F 2002/9665; A61F 2/958; A61F 2/9522; A61F 2002/9505; A61F 2/9517; A61F 2/962; A61F 2/95; A61M 25/0074
See application file for complete search history.

(56) References Cited

U.S. PATENT DOCUMENTS

| 4,249,536 | A | * | 2/1981 | Vega | ................. | A61M 25/0068 604/95.01 |
| 5,026,377 | A |   | 6/1991 | Burton et al. | | |
| 5,290,295 | A |   | 3/1994 | Querals et al. | | |
| 5,683,451 | A |   | 11/1997 | Lenker et al. | | |

(Continued)

FOREIGN PATENT DOCUMENTS

| EP | 0696447 A2 | 10/1995 |
| JP | 2010527695 A | 8/2010 |

(Continued)

OTHER PUBLICATIONS

International Search Report and Written Opinion dated Jul. 10, 2019 for International Application No. PCT/US2019/026408.

*Primary Examiner* — Seema Mathew
(74) *Attorney, Agent, or Firm* — Seager, Tufte & Wickhem, LLP

(57) ABSTRACT

A stent delivery device having a delivery configuration for delivering a stent to a treatment location and a deployment configuration for deploying the stent at the treatment location may include an outer sheath, an inner shaft slidably disposed within a lumen of the outer sheath, and a distal tip member fixedly attached to a distal end of the inner shaft. A distal portion of the outer sheath may include a plurality of longitudinal strips circumferentially disposed about the lumen of the outer sheath. At least a portion of the distal tip member may be configured to slide over a distal end of the outer sheath in the delivery configuration.

17 Claims, 11 Drawing Sheets

(56) References Cited

U.S. PATENT DOCUMENTS

| | | | |
|---|---|---|---|
| 5,702,419 A * | 12/1997 | Berry | A61F 2/91 623/1.13 |
| 5,735,859 A * | 4/1998 | Fischell | A61F 2/95 606/198 |
| 5,800,517 A | 9/1998 | Anderson et al. | |
| 5,824,041 A | 10/1998 | Lenker et al. | |
| 6,024,763 A | 2/2000 | Lenker et al. | |
| 6,126,685 A | 10/2000 | Lenker et al. | |
| 6,132,458 A | 10/2000 | Staehle et al. | |
| 6,149,680 A | 11/2000 | Shelso et al. | |
| 6,187,016 B1 | 2/2001 | Hedges et al. | |
| 6,350,278 B1 | 2/2002 | Lenker et al. | |
| 6,355,060 B1 | 3/2002 | Lenker et al. | |
| 6,391,050 B1 | 5/2002 | Broome | |
| 6,464,683 B1 | 10/2002 | Samuelson et al. | |
| 6,514,280 B1 | 2/2003 | Gilson | |
| 6,521,132 B2 | 2/2003 | Hughes | |
| 6,602,280 B2 | 8/2003 | Chobotov | |
| 6,607,551 B1 | 8/2003 | Sullivan et al. | |
| 6,676,693 B1 | 1/2004 | Belding et al. | |
| 6,902,575 B2 | 6/2005 | Laakso et al. | |
| 6,926,732 B2 | 8/2005 | Derus et al. | |
| 6,951,570 B2 | 10/2005 | Linder et al. | |
| 6,991,646 B2 | 1/2006 | Clerc et al. | |
| 7,127,789 B2 | 10/2006 | Stinson | |
| 7,758,624 B2 | 7/2010 | Dorn et al. | |
| 7,918,880 B2 | 4/2011 | Austin | |
| 7,947,070 B2 | 5/2011 | Headley et al. | |
| 8,088,154 B2 * | 1/2012 | Hoffman | A61F 2/95 623/1.11 |
| 8,206,427 B1 | 6/2012 | Ryan et al. | |
| 8,317,854 B1 | 11/2012 | Ryan et al. | |
| 8,359,721 B2 | 1/2013 | Melsheimer et al. | |
| 8,372,132 B2 | 2/2013 | Shin et al. | |
| 8,372,133 B2 | 2/2013 | Douk et al. | |
| 8,468,667 B2 | 6/2013 | Straubinger et al. | |
| 8,652,198 B2 | 2/2014 | Andreas et al. | |
| 8,668,728 B2 | 3/2014 | Headley et al. | |
| 8,702,780 B2 | 4/2014 | Hartley et al. | |
| 8,709,060 B2 | 4/2014 | Osborne | |
| 8,845,712 B2 * | 9/2014 | Irwin | A61F 2/97 623/1.11 |
| 8,998,980 B2 | 4/2015 | Shipley et al. | |
| 9,254,371 B2 | 2/2016 | Martin et al. | |
| 9,265,639 B2 | 2/2016 | Schneider et al. | |
| 9,622,895 B2 | 4/2017 | Cohen et al. | |
| 2001/0056295 A1 * | 12/2001 | Solem | A61F 2/95 623/1.11 |
| 2002/0052641 A1 * | 5/2002 | Monroe | A61M 25/001 623/1.11 |
| 2002/0120277 A1 | 8/2002 | Hauschild et al. | |
| 2003/0065352 A1 * | 4/2003 | Yang | A61M 29/02 604/103.1 |
| 2003/0139795 A1 | 7/2003 | Olson | |
| 2003/0149467 A1 * | 8/2003 | Linder | A61F 2/97 606/108 |
| 2004/0064179 A1 | 4/2004 | Linder et al. | |
| 2005/0033403 A1 * | 2/2005 | Ward | A61F 2/95 623/1.11 |
| 2006/0184226 A1 * | 8/2006 | Austin | A61F 2/95 623/1.11 |
| 2007/0239252 A1 * | 10/2007 | Hopkins | A61F 2/95 623/1.11 |
| 2007/0270932 A1 | 11/2007 | Headley et al. | |
| 2008/0082083 A1 * | 4/2008 | Forde | A61F 2/95 604/527 |
| 2008/0132989 A1 * | 6/2008 | Snow | A61F 2/966 623/1.42 |
| 2008/0255580 A1 * | 10/2008 | Hoffman | A61F 2/97 606/108 |
| 2009/0082840 A1 | 3/2009 | Rusk et al. | |
| 2009/0171434 A1 | 7/2009 | Rusk et al. | |
| 2009/0287290 A1 | 11/2009 | Macaulay et al. | |
| 2011/0082464 A1 | 4/2011 | Douk et al. | |
| 2011/0178588 A1 * | 7/2011 | Haselby | A61F 2/9661 623/1.11 |
| 2011/0251665 A1 * | 10/2011 | Schmitt | A61F 2/966 623/1.11 |
| 2011/0264191 A1 * | 10/2011 | Rothstein | A61F 2/2436 623/1.11 |
| 2012/0172962 A1 | 7/2012 | Nam et al. | |
| 2012/0172964 A1 | 7/2012 | Schneider et al. | |
| 2013/0110223 A1 | 5/2013 | Musinger et al. | |
| 2013/0123897 A1 | 5/2013 | Robinson | |
| 2015/0105849 A1 * | 4/2015 | Cohen | A61F 2/9524 623/1.12 |
| 2015/0257910 A1 * | 9/2015 | Duong | A61F 2/844 623/1.11 |
| 2016/0106562 A1 * | 4/2016 | Puckett, Jr. | A61F 2/966 606/108 |
| 2017/0135834 A1 | 5/2017 | Tassoni, Jr. et al. | |
| 2017/0290692 A1 * | 10/2017 | Toner | A61F 2/97 |
| 2018/0014957 A1 | 1/2018 | Harris et al. | |
| 2019/0350645 A1 * | 11/2019 | Montague | A61B 18/1482 |

FOREIGN PATENT DOCUMENTS

| | | |
|---|---|---|
| JP | 2014090969 A | 5/2014 |
| WO | 2010027485 A1 | 3/2010 |

* cited by examiner

STENT DELIVERY SYSTEM WITH REDUCED DEPLOYMENT FORCE

CROSS-REFERENCE TO RELATED APPLICATIONS

This application claims the benefit of priority under 35 U.S.C. § 119 of U.S. Provisional Application No. 62/654,984, filed Apr. 9, 2018, the entire disclosure of which is hereby incorporated by reference.

TECHNICAL FIELD

The present disclosure pertains to stents and methods for using stents. More particularly, the present disclosure pertains to aspects of stent delivery devices and means of deploying stents from stent delivery devices.

BACKGROUND

Delivery devices for expandable stents, such as those used in endoscopic applications, generally have an outer sheath that constrains the expandable stent in a radially contracted, delivery state. The self-expanding stent can be freed from the restraint of the outer sheath by removing the outer sheath from the constrained stent, allowing the expandable stent to expand to a radially expanded, deployed state. For example, the outer sheath may be withdrawn proximally relative to the stent and/or the stent may be pushed distally relative to the outer shaft, such as with an inner shaft movably positioned within the outer sheath. Once unconstrained by the outer sheath, the self-expanding stent can expand to force itself against the luminal wall of the body lumen. As delivery devices are made smaller to accommodate use in narrower body lumens and/or through other medical devices, such as endoscopes for example, physical constraints may result in an undesired increase in the amount of force required to deploy the stent. Accordingly, there is an ongoing need for improvements in catheters, devices, and/or systems that deliver self-expanding stents.

SUMMARY

In a first aspect, a stent delivery device having a delivery configuration for delivering a stent to a treatment location and a deployment configuration for deploying the stent at the treatment location may comprise an outer sheath, an inner shaft slidably disposed within a lumen of the outer sheath, and a distal tip member fixedly attached to a distal end of the inner shaft. A distal portion of the outer sheath may include a plurality of longitudinal strips circumferentially disposed about the lumen of the outer sheath. At least a portion of the distal tip member may be configured to slide over a distal end of the outer sheath in the delivery configuration.

In addition or alternatively, and in a second aspect, the plurality of longitudinal strips are defined by a plurality of slits extending at least partially through a wall of the distal portion of the outer sheath.

In addition or alternatively, and in a third aspect, the plurality of slits extend completely through the wall of the distal portion of the outer sheath.

In addition or alternatively, and in a fourth aspect, the plurality of longitudinal strips are defined by a plurality of weakened areas of a wall of the distal portion of the outer sheath, the plurality of weakened areas extending in a generally longitudinal direction along the distal portion of the outer sheath.

In addition or alternatively, and in a fifth aspect, distal translation of the distal tip member relative to the outer sheath is configured to shift the stent delivery device from the delivery configuration toward the deployment configuration.

In addition or alternatively, and in a sixth aspect, in the deployment configuration, the distal tip member is spaced distally apart from the distal end of the outer sheath.

In addition or alternatively, and in a seventh aspect, an outer surface of the outer sheath tapers inwardly toward the distal end of the outer sheath.

In addition or alternatively, and in an eighth aspect, the plurality of longitudinal strips each have a generally uniform length.

In addition or alternatively, and in a ninth aspect, at least one of the plurality of longitudinal strips has a length different from another one of the plurality of longitudinal strips.

In addition or alternatively, and in a tenth aspect, the plurality of longitudinal strips are oriented helically about the lumen of the outer sheath.

In addition or alternatively, and in an eleventh aspect, a stent delivery device having a delivery configuration and a deployment configuration may comprise an outer sheath, an inner shaft slidably disposed within a lumen of the outer sheath, and a distal tip member fixedly attached to a distal end of the inner shaft. The stent delivery device, in the delivery configuration, may be configured to house a stent in a collapsed configuration radially between the inner shaft and a distal portion of the outer sheath. The distal portion of the outer sheath includes a plurality of longitudinal strips circumferentially disposed about the lumen of the outer sheath. A proximal portion of the distal tip member may be configured to circumferentially surround a distal end of the outer sheath in the delivery configuration, thereby retaining the stent in the collapsed configuration. In the deployment configuration, the plurality of longitudinal strips are configured to radially expand, thereby permitting a distal portion of the stent to expand toward an expanded configuration.

In addition or alternatively, and in a twelfth aspect, a proximal portion of the stent is retained in the collapsed configuration by the outer sheath proximal of the radially expanded longitudinal strips.

In addition or alternatively, and in a thirteenth aspect, the stent is biased radially outward against an inner surface of the distal portion of the outer sheath in the delivery configuration.

In addition or alternatively, and in a fourteenth aspect, the plurality of longitudinal strips are self-biased radially inward toward an equilibrium position when a radially outward force against the plurality of longitudinal strips is absent.

In addition or alternatively, and in a fifteenth aspect, the distal tip member circumferentially surrounds a distal end region of the stent in the delivery configuration.

In addition or alternatively, and in a sixteenth aspect, a stent delivery system may comprise an outer sheath, wherein the outer sheath comprises a plurality of longitudinal strips extending proximally from the distal end of the outer sheath; an inner shaft slidably disposed within a lumen of the outer sheath; a self-expanding stent disposed radially between the inner shaft and the outer sheath in a radially collapsed configuration and exerting a radially outward force against an inner surface of the outer sheath; and a distal tip member fixedly attached to a distal end of the inner shaft and moveable between a delivery configuration in which a proximal portion of the distal tip member circumferentially encompasses a distal end of the outer sheath and a deployment configuration in which the distal tip member is positioned distal of the distal end of the outer sheath. In the deployment configuration, the plurality of longitudinal strips are urged radially outward by the radially outward force of the stent to a radially outward position to permit a distal portion of the stent to radially expand. The plurality of longitudinal strips are biased to assume an equilibrium position when not subjected to the radially outward force exerted by the stent, the radially outward position being radially outward of the equilibrium position.

In addition or alternatively, and in a seventeenth aspect, after the distal portion of the stent radially expands, a proximal portion of the stent is retained within the outer sheath proximal of the plurality of longitudinal strips.

In addition or alternatively, and in an eighteenth aspect, after the distal portion of the stent radially expands, proximal retraction of the outer sheath relative to the stent releases the proximal portion of the stent.

In addition or alternatively, and in a nineteenth aspect, in the equilibrium position, the plurality of longitudinal strips do not extend radially outward of an outer surface of the outer sheath proximal of the plurality of longitudinal strips.

In addition or alternatively, and in a twentieth aspect, in the delivery configuration, at least a portion of the stent is circumferentially encompassed by the proximal portion of the distal tip member.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
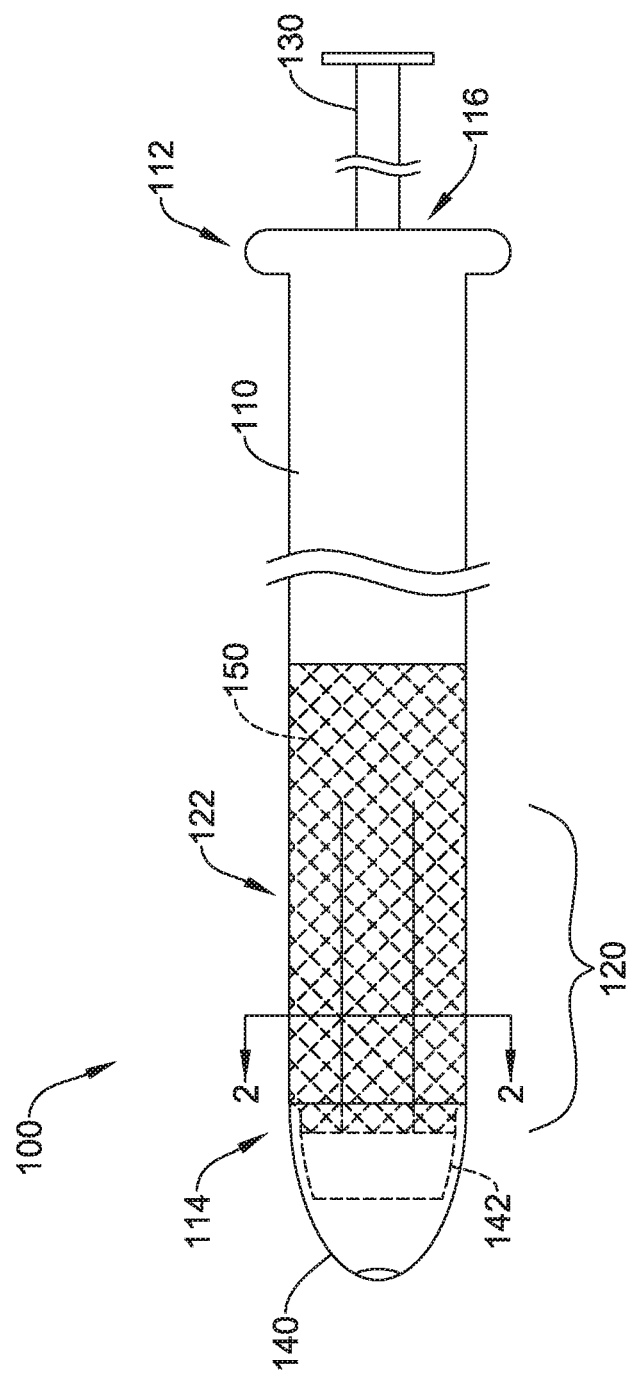
FIG. 1 illustrates aspects of an example endoscopic stent system in a delivery configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 illustrates an example stent delivery system. The stent delivery system may include a stent delivery device 100 having a delivery configuration (e.g., FIG. 1) for delivering a stent 150 to a treatment location and a deployment configuration for deploying the stent 150 at the treatment location. The stent delivery device 100 may include an outer sheath 110, an inner shaft 130 slidably disposed within a lumen 116 of the outer sheath 110, and a distal tip member 140 fixedly attached to a distal end of the inner shaft 130.

In some embodiments, the outer sheath 110 may be sized and configured for passage through an endoscope or other medical device. In some embodiments, the outer sheath 110 may be a tubular structure including a wall having an outer surface and an inner surface defining the lumen 116. The outer sheath 110 and/or the lumen 116 of the outer sheath 110 may be sized and configured to house a stent 150 in a radially collapsed or constrained configuration. For example, a distal region of the outer sheath 110 may surround the expandable stent 150 to retain the stent 150 in a radially constrained state during delivery of the stent 150 to a target site in a body lumen.

The outer sheath 110 may include a proximal end 112, a distal end 114, and a distal portion 120 proximate the distal end 114. The distal portion 120 may be configured to radially expand to facilitate deployment of the stent 150 at a target location. For example, the distal portion 120 of the outer sheath 110 may include a plurality of longitudinal strips 122 circumferentially disposed about the lumen 116 of the outer sheath 110, and thus circumferentially arranged about the stent 150. The plurality of longitudinal strips 122 may extend to the distal end 114 of the outer sheath 110 such that the distal region of the outer sheath 110, including the distal end 114 may have a discontinuous circumferential wall surrounding the distal portion of the stent 150. Additional details related to the distal portion 120 of the outer sheath 110, and namely the plurality of longitudinal strips 122 will be discussed herein.

In some embodiments, the outer surface of the outer sheath 110 tapers inwardly toward the distal end 114 of the outer sheath 110. For example, an outer extent or diameter at a distalmost end of the outer sheath 110 may be less than an outer extent or diameter of the outer sheath 110 at the proximal end 112 and/or at locations therebetween. For example, the outer extent or diameter at the distalmost end of the outer sheath 110 may be less than the outer extent or diameter of the outer sheath 110 surrounding a proximal portion of the stent 150. In some embodiments, the distal end 114 may include a narrowed generally cylindrical portion having an outer extent or diameter less than the outer extent or diameter of the outer sheath 110 proximal of the narrowed generally cylindrical portion at the distal end 114. For example, the distal end 114 may include a stepped feature and/or may be offset radially inward from and generally parallel to the outer surface of the outer sheath 110 proximal of the narrowed generally cylindrical portion at the distal end 114. In some embodiments, the proximal end 112 of the outer sheath 110 may include an enlarged flange, a hub, a handle, and/or other suitable means for handling and/or manipulating the outer sheath 110. In at least some embodiments, the lumen 116 of the outer sheath 110 may extend from (and/or through) the proximal end 112 of the outer sheath 110 to (and/or through) the distal end 114 of the outer sheath 110. Some suitable but non-limiting materials for the outer sheath 110, for example metallic materials, polymer materials, composite materials, synthetic materials, etc., are described below.

In some embodiments, the inner shaft 130 may be and/or include a solid shaft, a tubular member such as a hypotube, catheter, etc., and/or combinations thereof. In some instances, the inner shaft 130 may include a guidewire lumen for advancing the stent delivery device 100 over a guidewire to a treatment location. In some embodiments, a proximal end of the inner shaft 130 may include an enlarged flange, a hub, a handle, and/or other suitable means for handling and/or manipulating the inner shaft 130 relative to the outer sheath 110. The inner shaft 130 may be axially, longitudinally, slidably, and/or rotatably disposed within the lumen 116 of the outer sheath 110. In at least some embodiments, the inner shaft 130 may be positioned coaxially within the outer sheath 110. Some suitable but non-limiting materials for the inner shaft 130, for example metallic materials, polymer materials, composite materials, synthetic materials, etc., are described below.

The stent delivery device 100 may include the distal tip member 140 fixedly attached to the distal end of the inner shaft 130. The distal tip member 140 may be moveable relative to the distal end 114 of the outer shaft 110 between the delivery configuration and the deployment configuration. In some embodiments, at least a portion of the distal tip member 140 may be configured to slide over the distal end 114 of the outer sheath 110 and/or the plurality of longitudinal strips 122 in the delivery configuration. For example, at least a proximal portion of the distal tip member 140 may axially and/or longitudinally overlap the distal end 114 of the outer sheath 110 and/or the plurality of longitudinal strips 122 in the delivery configuration. In some embodiments, a proximal portion of the distal tip member 140 may be configured to circumferentially surround the distal end 114 of the outer sheath 110 and/or the distal ends of the plurality of longitudinal strips 122 in the delivery configuration. In some embodiments, in the delivery configuration, the proximal portion of the distal tip member 140 may be configured to circumferentially encompass the distal end 114 of the outer sheath 110 and/or the distal ends of the plurality of longitudinal strips 122.

In some embodiments, the distal tip member 140 may include a lumen extending therethrough. In some embodiments, the inner shaft 130 may be disposed within the lumen through the distal tip member 140. In some embodiments, the inner shaft 130 may be in fluid communication with the lumen through the distal tip member 140. In at least some embodiments, the distal tip member 140 may include and/or be formed with an atraumatic shape. In some embodiments, an outermost shape and/or cross-sectional profile of the distal tip member 140 may be similar to and/or may align with an outer shape and/or a cross-sectional profile of the outer sheath 110.

Figure 7A:
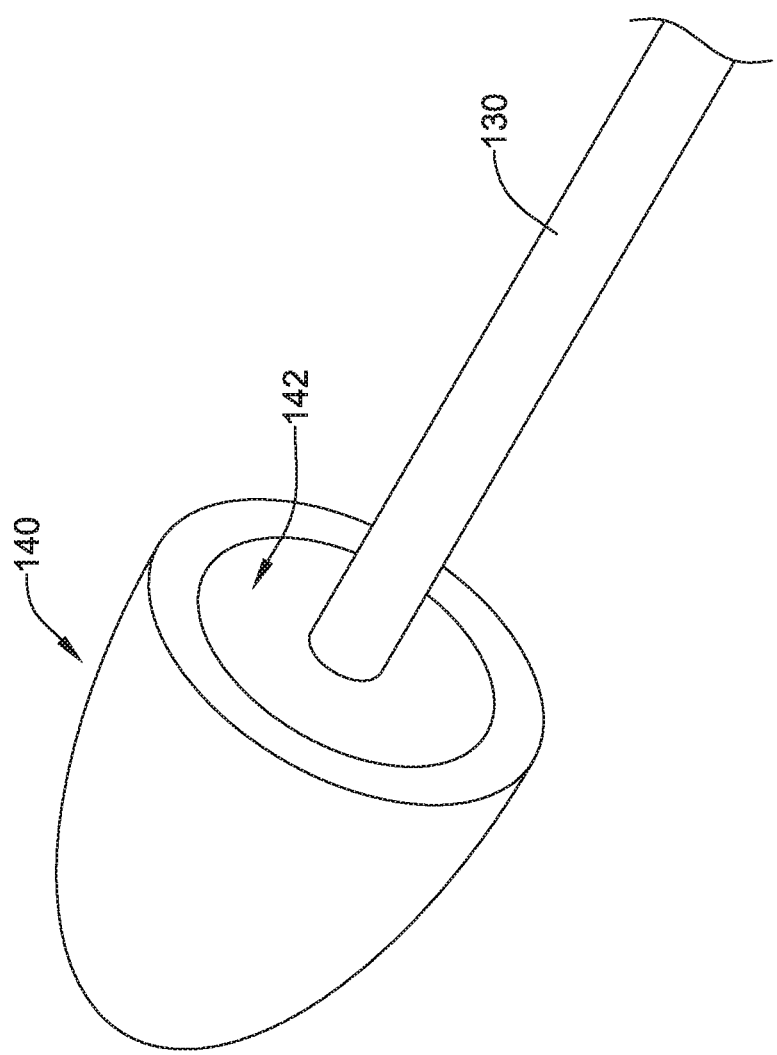
FIG. 7A illustrates an exemplary configuration of a distal tip member.
Figure 7B:
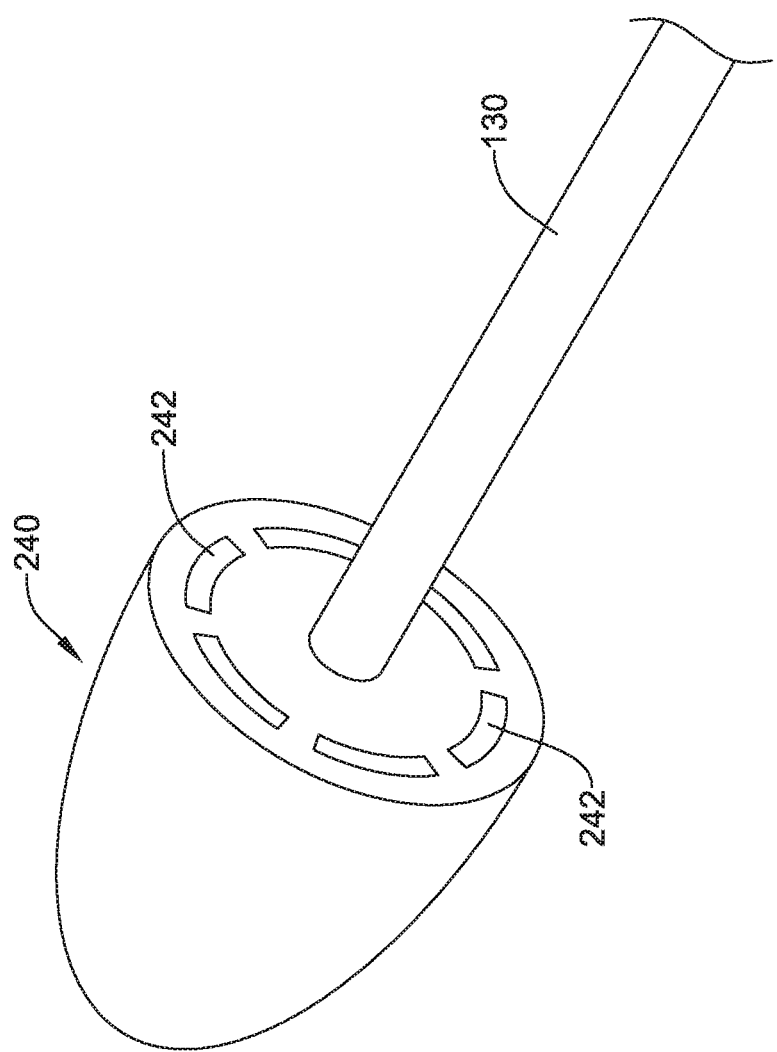
FIG. 7B illustrates an alternative configuration of a distal tip member.

In some embodiments, the distal tip member 140 may have a generally solid distal portion and a generally hollow proximal portion. The generally hollow proximal portion of the distal tip member 140 may be sized, shaped, and configured to accept, slide over, circumferentially surround, and/or circumferentially encompass the distal end 114 of the outer sheath 110 and/or the distal ends of the plurality of longitudinal strips 122 therein in the delivery configuration. For example, the distal end 114 of the outer sheath 110 and/or the distal ends of the plurality of longitudinal strips 122 may be positioned within and/or inside of the proximal portion of the distal tip member 140 in the delivery configuration. As shown in FIG. 7A, in some instances the distal tip member 140 may include a cavity 142, extending into the distal tip member 140 from the proximal end of the distal tip member 140. The distal ends of the longitudinal strips 122 may be positioned in the cavity 142 in the delivery configuration such that the proximal portion of the distal tip member 140 surrounds the distal ends of the longitudinal strips 122. In other instances, as shown in FIG. 7B, the distal tip member 140 may include a plurality of cavities 242 extending into the distal tip member 140 from the proximal end of the distal tip member 140. Each cavity 242 may receive the distal end of one of the longitudinal strips 122, for example, in the delivery configuration such that the proximal portion of the distal tip member 140 surrounds the distal ends of the longitudinal strips 122. Some suitable but non-limiting materials for the distal tip member 140, for example metallic materials, polymer materials, composite materials, synthetic materials, etc., are described below.

The stent 150, which may be a self-expanding stent, may be configured to shift between a radially collapsed configuration when radially constrained and a radially expanded configuration when radially unconstrained. In some embodiments, the stent 150 may be biased toward the radially expanded configuration in an equilibrium state. In some embodiments, the stent 150 may be self-biased toward the radially expanded configuration. In some embodiments, the stent 150 may be formed by cutting or removing material from a unitary tubular member, such as by laser cutting or other suitable processes. In some embodiments, the stent 150 may be formed as a braided, woven, and/or knit stent from one or more wires, filaments, etc. The stent 150 may have an overall length suitable for the intended procedure and/or use. For example, the stent 150 may have an overall length ranging from less than 5 mm to more than 200 mm. In some embodiments, the stent 150 may be formed to an overall diameter or outer extent ranging from 1 mm to 30 mm, depending on the intended usage. Some suitable but non-limiting materials for the stent 150, for example metallic materials, polymer materials, composite materials, synthetic materials, etc., are described below.

The stent delivery device 100, in the delivery configuration, may be configured to retain the stent 150 in the radially collapsed configuration radially between the inner shaft 130 and the distal portion 120 of the outer sheath 110. In some embodiments, the stent 150 may be a self-expanding stent disposed radially between the inner shaft 130 and the distal portion 120 of the outer sheath 110 in the radially collapsed configuration and exerting a radially outward force against the inner surface of the distal portion 120 of the outer sheath 110. The stent 150 may be biased radially outward against the inner surface of the distal portion 120 of the outer sheath 110 in the delivery configuration of the stent delivery device 100 and/or the radially collapsed configuration of the stent 150.

In some embodiments, in the delivery configuration of the stent delivery device 100, at least a portion of the stent 150 may be circumferentially surrounded and/or encompassed by the proximal portion of the distal tip member 140. The distal tip member 140 may circumferentially surround and/or encompass a distal end region of the stent 150 in the delivery configuration of the stent delivery device 100. For example, in some embodiments, the distal tip member 140 may circumferentially surround and/or encompass at least a distalmost strut row of the stent 150, a distalmost circumferential band of the stent 150, a distalmost circumferential row of cells of the stent 150, and/or a first intersection of filaments proximal of the distal end of the stent 150. In some embodiments, the distal tip member 140 may circumferentially surround and/or encompass at least 1%, at least 5%, at least 10%, or at least 20% of the overall length of the stent 150 extending proximally from the distal end of the stent 150. In some embodiments, the distal tip member 140 may circumferentially surround and/or encompass at least 1 mm, at least 3 mm, at least 5 mm, or at least 10 mm of the overall length of the stent 150 extending proximally from the distal end of the stent 150.

As discussed herein, a distal portion 120 of the outer sheath 110 may include the plurality of longitudinal strips 122 circumferentially disposed about the lumen 116 of the outer sheath 110 and extending proximally from the distal end 114 of the outer sheath 110. The plurality of longitudinal strips 122 extend in a generally longitudinal direction along the distal portion 120 of the outer sheath 110. In some embodiments, the plurality of longitudinal strips 122 may comprise two longitudinal strips, three longitudinal strips, four longitudinal strips, five longitudinal strips, six longitudinal strips, seven longitudinal strips, eight longitudinal strips, nine longitudinal strips, ten longitudinal strips, or another number of longitudinal strips as desired.

Figure 2A:
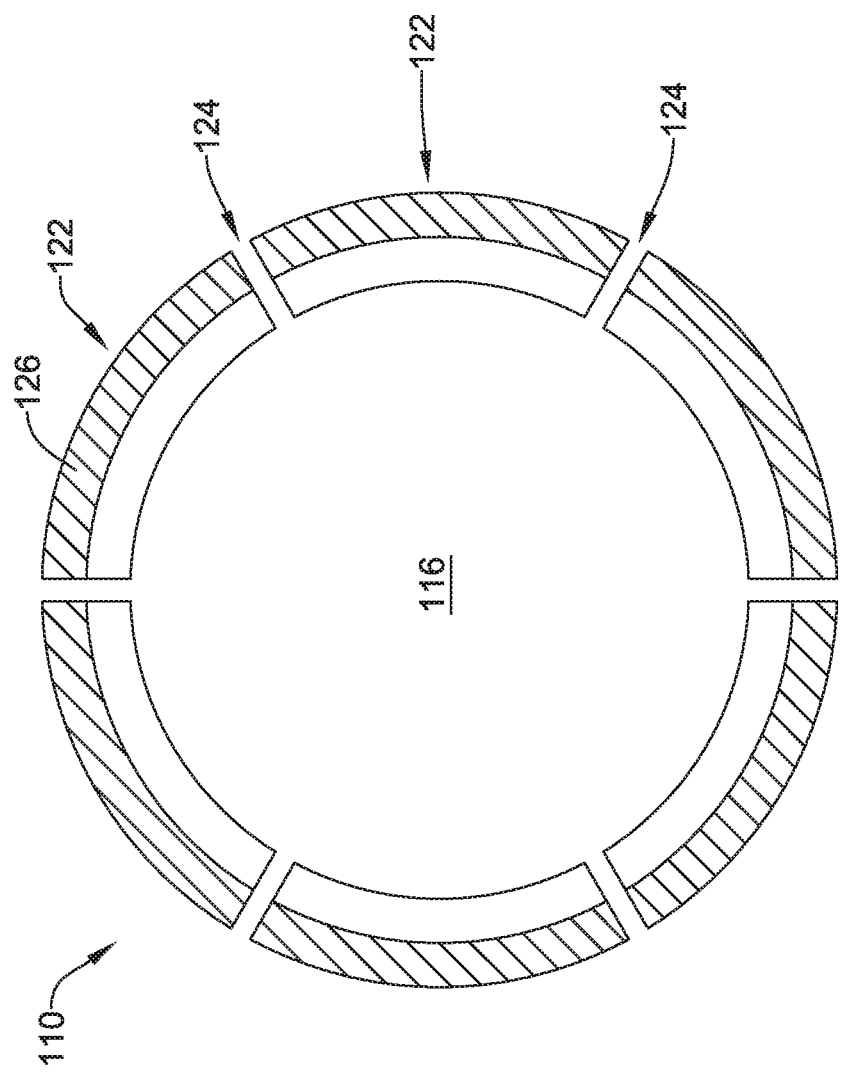
FIG. 2A is a partial cross-sectional view of an example outer sheath taken along the line 2-2 of FIG. 1.

In some embodiments, the plurality of longitudinal strips 122 are defined by a plurality of slits 124 extending at least partially through a wall 126 of the distal portion 120 of the outer sheath 110. In some embodiments, the plurality of slits 124 may extend completely through the wall 126 of the distal portion 120 of the outer sheath 110 from the outer surface of the outer sheath 110 to the lumen 116 of the outer sheath 110, as seen in cross-section in FIG. 2A for example. The plurality of slits 124 between adjacent longitudinal strips 122 may extend to the distal end 114 of the outer sheath 110, such that each of the longitudinal strips 122 has a proximal end or base attached to the remainder of the outer sheath 110 and a free distal end configured to move relative to the distal ends of the other longitudinal strips 122. In order to enhance understanding of the outer sheath 110, other features shown in FIG. 1 are hidden from view in FIG. 2A. While opposing sides of the plurality of longitudinal strips 122 are illustrated in FIG. 2A as being spaced apart from each other in the delivery configuration, in some embodiments, opposing sides of the plurality of longitudinal strips 122 may abut and/or be in contact with each other in the delivery configuration. Other configurations, including combinations thereof, are also contemplated.

Figure 2B:
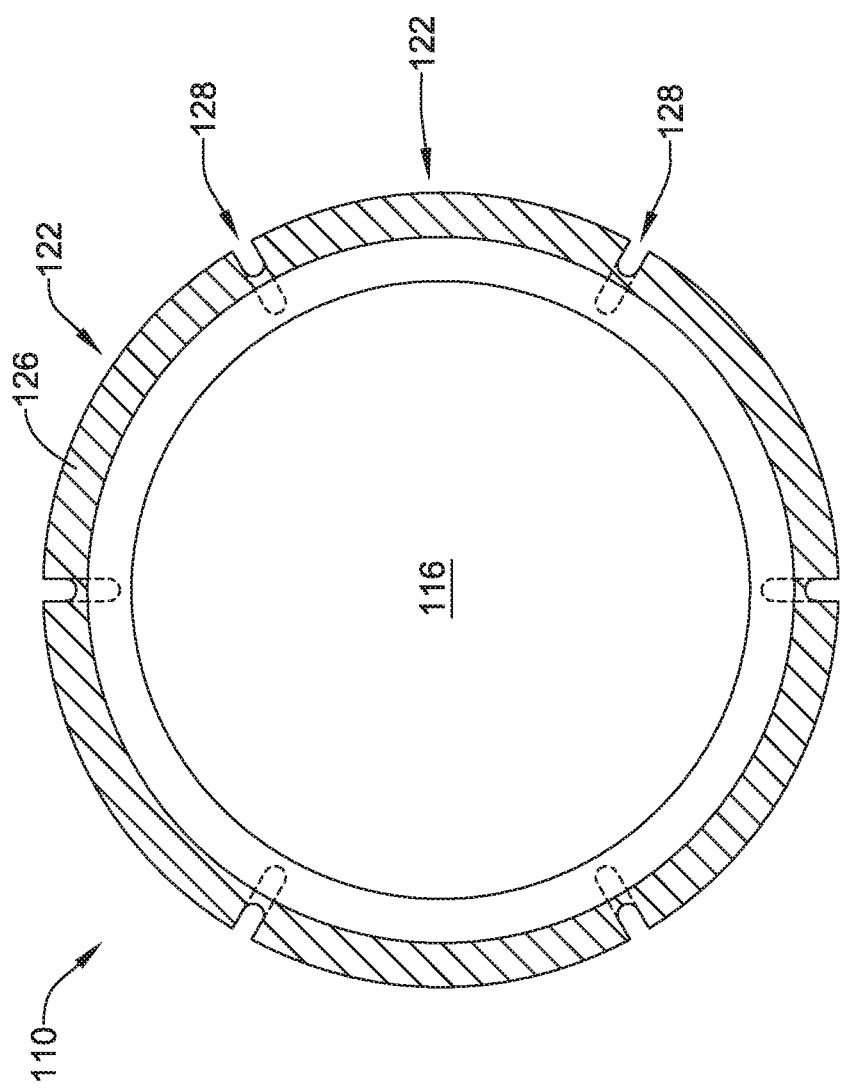
FIG. 2B is a partial cross-sectional view of an example outer sheath taken along the line 2-2 of FIG. 1.

In some embodiments, the plurality of longitudinal strips 122 may be defined by a plurality of weakened areas 128 of the wall 126 of the distal portion 120 of the outer sheath 110, the plurality of weakened areas 128 extending in a generally longitudinal direction along the distal portion 120 of the outer sheath 110. In some instances, the weakened areas 128 may be grooves, notches thinned regions, etc. extending only through a portion of the thickness of the wall of the outer sheath 110. In some embodiments, the plurality of weakened areas 128 may be formed in the outer surface of the outer sheath 110, as shown in cross-section in FIG. 2B for example. In order to enhance understanding of the outer sheath 110, other features shown in FIG. 1 are hidden from view in FIG. 2B. Alternatively, in some embodiments, the plurality of weakened areas 128 may be formed in the inner surface of the outer sheath 110, or the plurality of weakened areas 128 may be formed in various combinations in the inner and outer surfaces of the outer sheath 110.

In some embodiments, the plurality of weakened areas 128 may fail to compromise the fluid-tightness of the outer sheath 110. For example, in some embodiments of the outer sheath 110 having the plurality of weakened areas 128, the wall 126 of the outer sheath 110 may be continuous and/or free from holes, apertures, slots, slits, cuts, etc. along its entire length and the plurality of weakened areas 128 may not extend completely through the wall 126 of the outer sheath 110 to the lumen 116 of the outer sheath 110. In some embodiments, the plurality of weakened areas 128 may extend partially through the wall 126 of the outer sheath 110 and/or may reduce a thickness of the wall 126 of the outer sheath 110 at the plurality of weakened areas 128. In some embodiments, the plurality of weakened areas 128 may be formed as score marks in the inner surface or outer surface of the outer sheath 110. In some alternative embodiments, the plurality of weakened areas 128 may be formed as a perforation in the wall 126 of the outer sheath 110. Other forms of weakened areas that may facilitate easy tearing, frangibility, and/or separating of the wall 126 of the outer sheath 110 to form and/or define the plurality of longitudinal strips 122 are also contemplated.

Figure 3:
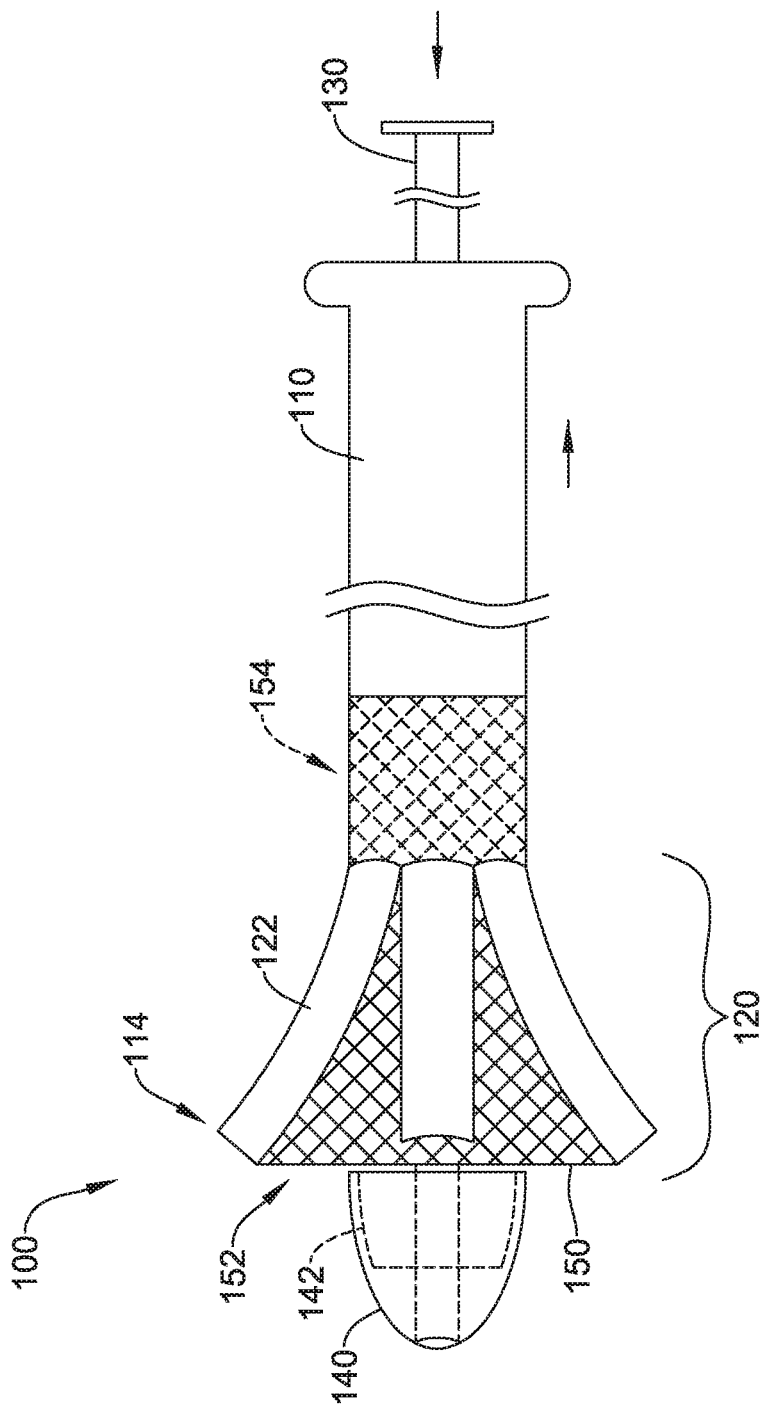
FIGS. 3-4 illustrate aspects of the example endoscopic stent system of FIG. 1 deploying an example stent.

As seen in FIG. 3, distal translation of the inner shaft 130 and/or the distal tip member 140 relative to the outer sheath 110 (or proximal translation of the outer sheath 130 relative to the inner shaft 130 and/or the distal tip member 140) may be configured to shift the stent delivery device 100 from the delivery configuration toward the deployment configuration. In the deployment configuration, the distal tip member 140 may be spaced distally apart from the distal end 114 of the outer sheath 110. Thus, distal translation of the inner shaft 130 and/or the distal tip member 140 relative to the outer sheath 110 (or proximal translation of the outer sheath 130 relative to the inner shaft 130 and/or the distal tip member 140) may release the distal ends of the longitudinal strips 122 from the cavity 142 or cavities 242 of the distal tip member 140, freeing the distal ends of the longitudinal strips 122 to radially expand under the radially outward force exerted by the stent 150. As discussed herein, the stent 150 may exert a radially outward force against the inner surface of the distal portion 120 of the outer sheath 110. In the deployment configuration, the plurality of longitudinal strips 122 are configured to radially expand, thereby permitting a distal portion 152 of the stent 150 to expand toward the expanded configuration. For example, in the deployment configuration, the plurality of longitudinal strips 122 are urged radially outward by the radially outward force of the stent 150 to a radially outward position to permit the distal portion 152 of the stent 150 to radially expand.

Figure 4:
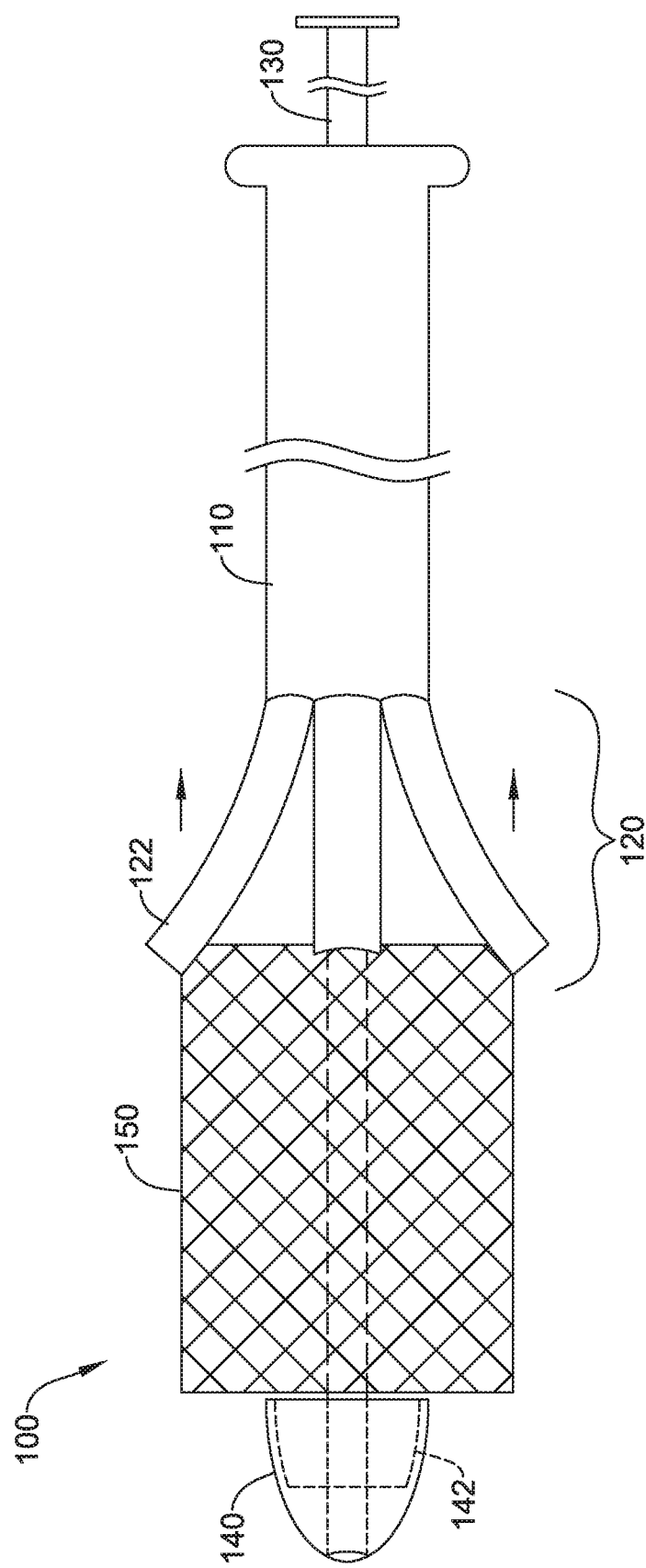

After the distal portion 152 of the stent 150 radially expands, a proximal portion 154 of the stent 150 is retained in the radially collapsed configuration within the outer sheath 110 proximal of the plurality of longitudinal strips 122. For example, the proximal portion 154 of the stent 150 is retained in the collapsed configuration by the outer sheath 110 proximal of the radially expanded plurality of longitudinal strips 122. In some embodiments, the proximal portion 154 of the stent 150 retained within the outer sheath 110 proximal of the plurality of longitudinal strips 122 may comprise about 10% or more, about 15% or more, about 20% or more, about 25% or more, or about 50% or more of the overall length of the stent 150. After the distal portion 152 of the stent 150 radially expands, proximal translation and/or retraction of the outer sheath 110 relative to the stent 150 and/or the inner shaft 130 may release the proximal portion 154 of the stent 150 from the outer sheath 110, as seen in FIG. 4 for example, thereby permitting the proximal portion 154 of the stent 150 to radially expand to the expanded configuration.

By configuring the stent delivery device 100 and/or the stent delivery system in this manner, the distal portion of the stent 150 may be radially expanded, and thus deployed while still holding, grasping, retaining, etc. a proximal portion of the stent 150 to permit repositioning and/or redeployment, if necessary. In addition or alternatively, frictional forces present due to the stent 150 being disposed within the lumen 116 of the outer sheath 110 in the collapsed configuration and exerting a radially outward force against the inner surface of the outer sheath 110 may be reduced because less of the overall length of the stent 150 must translate through the lumen 116 along the inner surface of the outer sheath 110 during deployment (e.g., during retraction of the outer sheath 110 relative to the stent 150.

Figure 5:
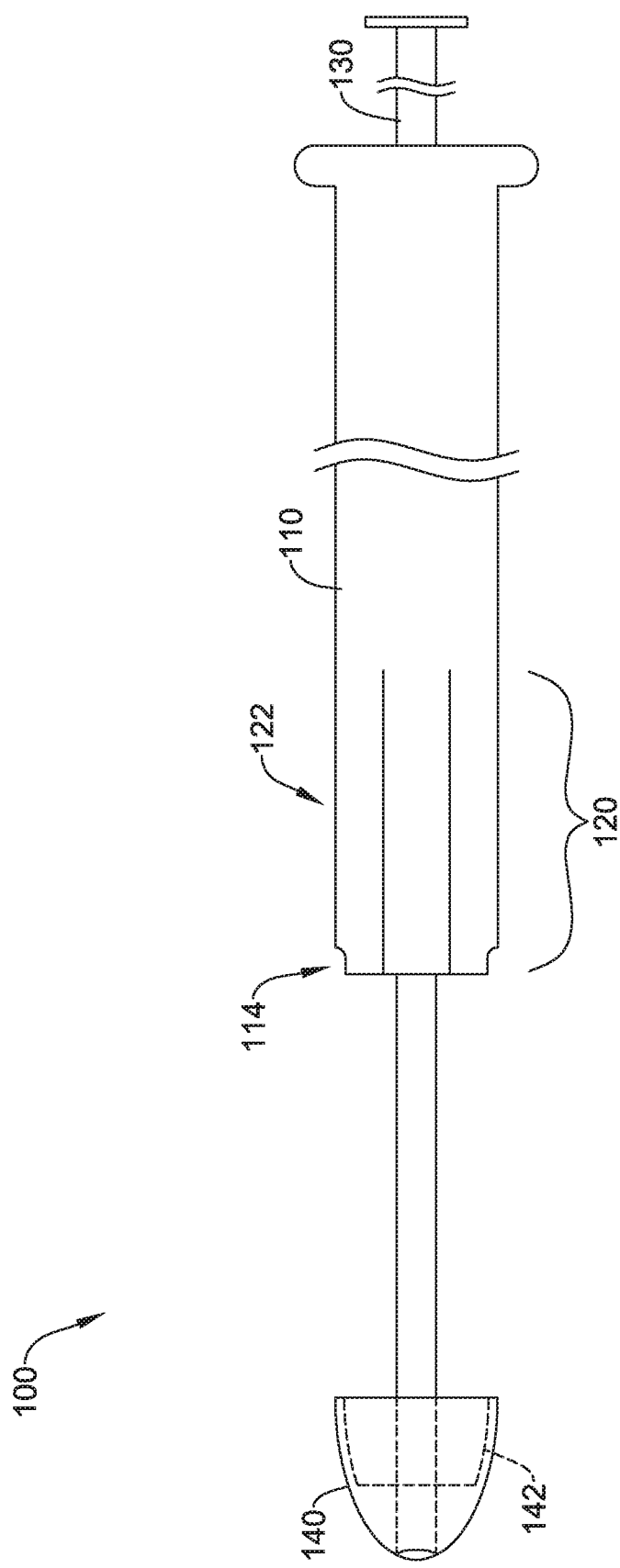
FIG. 5 illustrates aspects of an example outer sheath after deploying a stent.

Following proximal translation and/or retraction of the outer sheath 110 relative to the stent 150 and/or the inner shaft 130, and/or release of the proximal portion 154 of the stent 150, the plurality of longitudinal strips 122 may be biased to assume an equilibrium position when not subjected to the radially outward force exerted by the stent 150 against the inner surface of the outer sheath 110 and/or the plurality of longitudinal strips 122, as seen in FIG. 5 for example. In at least some embodiments, the plurality of longitudinal strips 122 are self-biased radially inward toward the equilibrium position when the radially outward force against the inner surface of the outer sheath 110 and/or the plurality of longitudinal strips 122 is absent. The radially outward position (e.g., FIG. 4) of the plurality of longitudinal strips 122 consequent the radial outward forces applied by the stent may be radially outward of the equilibrium position (e.g., FIG. 5). In some embodiments, in the equilibrium position, the plurality of longitudinal strips 122 do not extend radially outward of the outer surface of the outer sheath 110 proximal of the plurality of longitudinal strips 122. For example, an outer surface of the plurality of longitudinal strips 122 may be substantially parallel and/or axially in line with the outer surface of the outer sheath 110 proximal of the longitudinal strips 122, as seen in FIG. 5, such that in the equilibrium position the outer sheath 110 defines a substantially cylindrical outer surface proximal of the distal end 114. The radially inward bias of the plurality of longitudinal strips 122 may permit and/or facilitate shifting the stent delivery device 100 back to or toward the delivery configuration, wherein the distal tip member 140 slides over, circumferentially surrounds, and/or circumferentially encompasses the distal end 114 of the outer sheath 110 and/or the plurality of longitudinal strips 122 for withdrawal of the stent delivery device 100 from the treatment location after deployment of the stent 150.

Figure 6A:
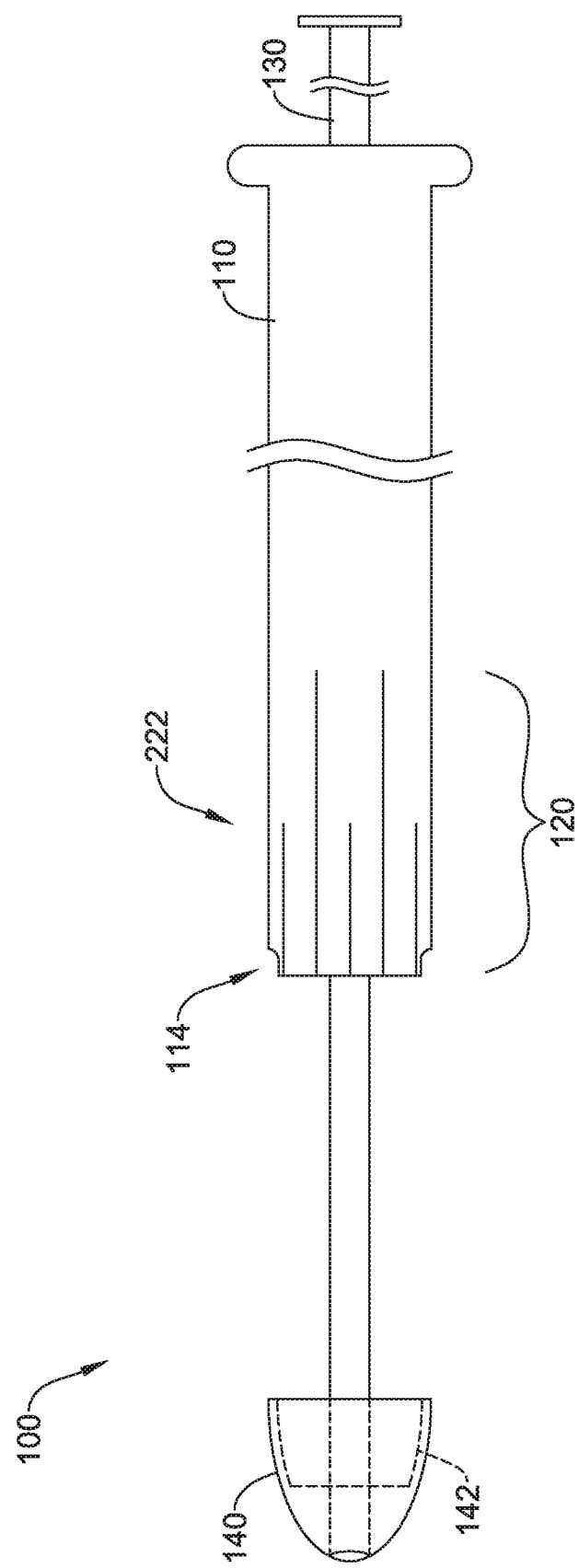
FIGS. 6A-6C illustrate alternative configurations of an example outer sheath.
Figure 6B:
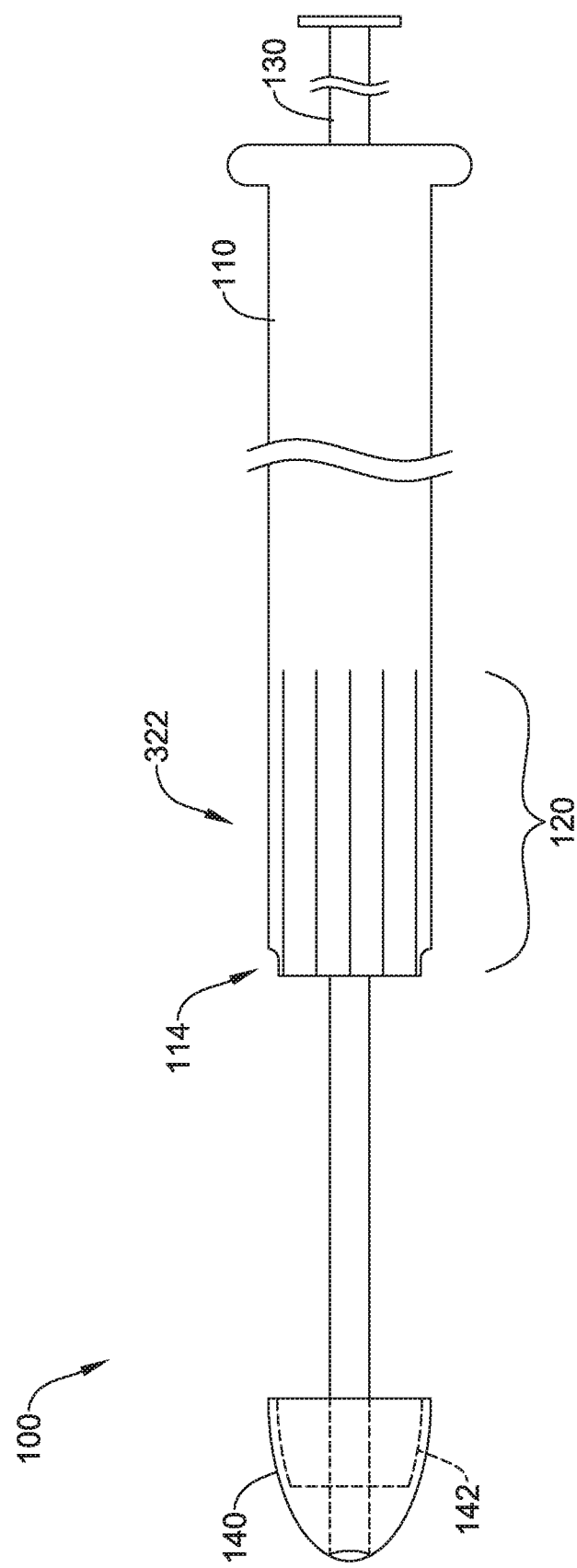
Figure 6C:
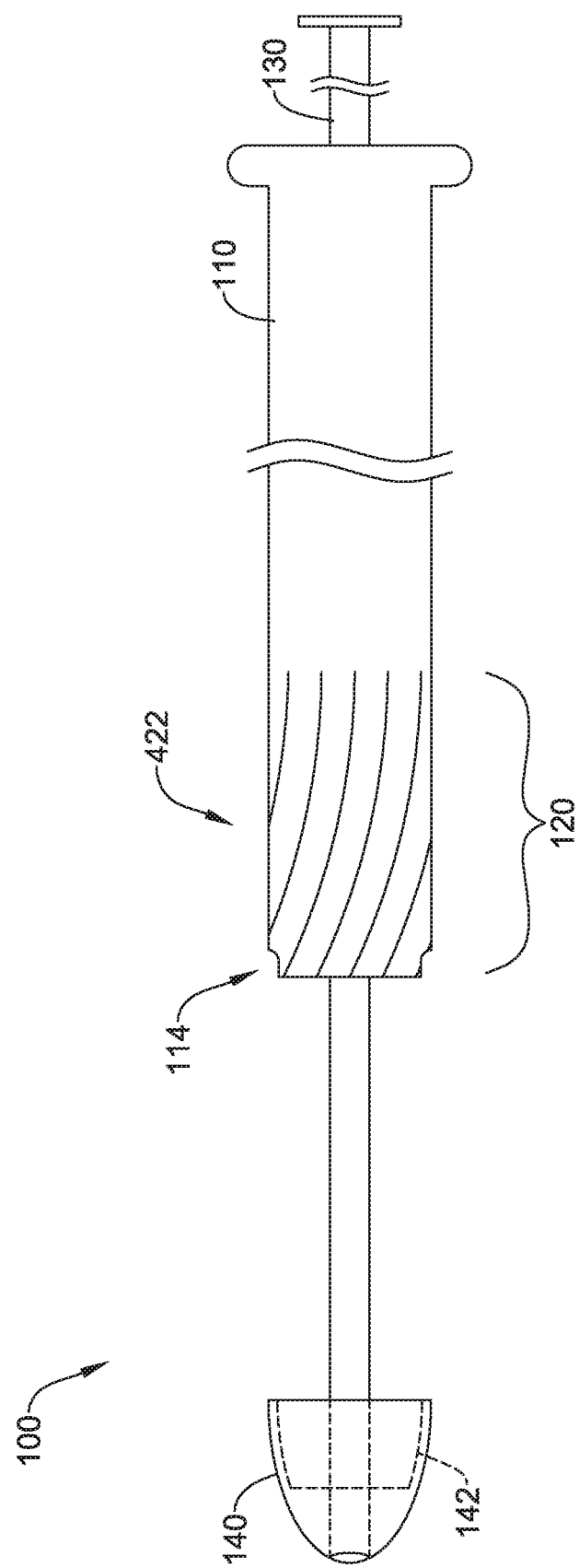

FIGS. 6A-6C illustrate several alternative configurations of the plurality of longitudinal strips 122. These alternative configurations may be used interchangeably within any embodiment(s) described herein and are not intended to be mutually exclusive. For example, certain aspects of the various configurations may be combined in some embodiments. For convenience and ease of understanding, the plurality of longitudinal strips are shown with unique reference numerals, all of which may be used interchangeably with the plurality of longitudinal strips 122.

In one example, the distal portion 120 of the outer sheath 110 may include a plurality of longitudinal strips 222, wherein at least one of the plurality of longitudinal strips 222 and/or slits between adjacent longitudinal strips 222 has a length different from another one of the plurality of longitudinal strips 222 and/or slits, as shown in FIG. 6A. In some embodiments, the length of each of the plurality of longitudinal strips 222 may vary from one longitudinal strip to the next. In some embodiments, the length of the plurality of longitudinal strips 222 and/or slits may alternate between shorter and longer lengths around the lumen 116 and/or the circumference of the outer sheath 110. Other patterns of varying lengths of longitudinal strips and/or slits are also contemplated.

In another example, the distal portion 120 of the outer sheath 110 may include a plurality of longitudinal strips 322 having a greater density and/or quantity of longitudinal strips, as shown in FIG. 6B, than in some other embodiments. In some embodiments, the density of longitudinal strips may vary around the lumen 116 and/or the circumference of the outer sheath 110. For example, in some embodiments, the distal portion 120 of the outer sheath 110 may include groups and/or pluralities of high-density longitudinal strips along with and/or alongside groups and/or pluralities of low-density longitudinal strips.

In another example, the distal portion 120 of the outer sheath 110 may include a plurality of longitudinal strips 422 oriented helically about the lumen 116 and/or the circumference of the outer sheath 110, as shown in FIG. 6C. In some embodiments, the plurality of longitudinal strips 422 may be oriented helically in a clockwise direction about the lumen 116 and/or the circumference of the outer sheath 110. In some embodiments, the plurality of longitudinal strips 422 may be oriented helically in a counterclockwise direction about the lumen 116 and/or the circumference of the outer sheath 110. Other configurations, including but not limited to an arrangement having a plurality of longitudinal strips that are partially helical and partially parallel to a central longitudinal axis of the lumen 116, are also contemplated.

The materials that can be used for the various components of the stent delivery device 100, the outer sheath 110, the inner shaft 130, the distal tip member 140, the stent 150, etc. (and/or other systems or components disclosed herein) and the various elements thereof disclosed herein may include those commonly associated with medical devices. For simplicity purposes, the following discussion makes reference to the stent delivery device 100, the outer sheath 110, the inner shaft 130, the distal tip member 140, the stent 150, etc. However, this is not intended to limit the devices and methods described herein, as the discussion may be applied to other elements, members, components, or devices disclosed herein, such as, but not limited to, the plurality of longitudinal strips 122/222/322/422, etc. and/or elements or components thereof.

In some embodiments, the stent delivery device 100, the outer sheath 110, the inner shaft 130, the distal tip member 140, the stent 150, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the stent delivery device 100, the outer sheath 110, the inner shaft 130, the distal tip member 140, the stent 150, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the stent delivery device 100, the outer sheath 110, the inner shaft 130, the distal tip member 140, the stent 150, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stent delivery device 100, the outer sheath 110, the inner shaft 130, the distal tip member 140, the stent 150, etc. to achieve the same result.

In some embodiments, a degree of Magnetic Resonance Imaging (MRI) compatibility is imparted into the stent delivery device 100, the outer sheath 110, the inner shaft 130, the distal tip member 140, the stent 150, etc. For example, the stent delivery device 100, the outer sheath 110, the inner shaft 130, the distal tip member 140, the stent 150, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The stent delivery device 100, the outer sheath 110, the inner shaft 130, the distal tip member 140, the stent 150, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the stent delivery device 100, the outer sheath 110, the inner shaft 130, the distal tip member 140, the stent 150, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DUREThan® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the stent delivery device 100, the outer sheath 110, the inner shaft 130, the distal tip member 140, the stent 150, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the stent delivery device 100, the outer sheath 110, the inner shaft 130, the distal tip member 140, the stent 150, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A stent delivery device having a delivery configuration for delivering a stent to a treatment location and a deployment configuration for deploying the stent at the treatment location, comprising:
   an outer sheath;
   an inner shaft slidably disposed within a lumen of the outer sheath; and
   a distal tip member fixedly attached to a distal end of the inner shaft;
   wherein a distal portion of the outer sheath includes a plurality of longitudinal strips circumferentially disposed about the lumen of the outer sheath, wherein an outer surface of the plurality of longitudinal strips defines an outermost surface of the stent delivery device;
   wherein at least a portion of the distal tip member is configured to slide longitudinally over a distal end of the outer sheath in the delivery configuration;
   wherein a length of the plurality of longitudinal strips alternates between shorter and longer lengths around a circumference of the outer sheath;
   wherein the plurality of longitudinal strips are self-biased radially inward toward an equilibrium position when a radially outward force against the plurality of longitudinal strips is absent and the distal tip member is longitudinally spaced apart from the plurality of longitudinal strips.

2. The stent delivery device of claim 1, wherein the plurality of longitudinal strips are defined by a plurality of slits extending at least partially through a wall of the distal portion of the outer sheath.

3. The stent delivery device of claim 2, wherein the plurality of slits extend completely through the wall of the distal portion of the outer sheath.

4. The stent delivery device of claim 1, wherein the plurality of longitudinal strips are defined by a plurality of weakened areas of a wall of the distal portion of the outer sheath, the plurality of weakened areas extending in a generally longitudinal direction along the distal portion of the outer sheath.

5. The stent delivery device of claim 1, wherein distal translation of the distal tip member relative to the outer sheath is configured to shift the stent delivery device from the delivery configuration toward the deployment configuration.

6. The stent delivery device of claim 5, wherein in the deployment configuration, the distal tip member is spaced distally apart from the distal end of the outer sheath.

7. The stent delivery device of claim 1, wherein an outer surface of the outer sheath tapers inwardly toward the distal end of the outer sheath.

8. A stent delivery device having a delivery configuration and a deployment configuration, comprising:
   an outer sheath;

an inner shaft slidably disposed within a lumen of the outer sheath; and a distal tip member fixedly attached to a distal end of the inner shaft;

wherein the stent delivery device, in the delivery configuration, is configured to house a stent in a collapsed configuration radially between the inner shaft and a distal portion of the outer sheath;

wherein the distal portion of the outer sheath includes a plurality of longitudinal strips circumferentially disposed about the lumen of the outer sheath, wherein an outer surface of the plurality of longitudinal strips defines an outermost surface of the stent delivery device;

wherein a proximal portion of the distal tip member is configured to circumferentially surround a distal end of the outer sheath in the delivery configuration, thereby retaining the stent in the collapsed configuration;

wherein in the deployment configuration, the distal tip member is longitudinally spaced apart from the distal end of the outer sheath and the plurality of longitudinal strips are configured to radially expand, thereby permitting a distal portion of the stent to expand toward an expanded configuration;

wherein the plurality of longitudinal strips are self-biased radially inward toward an equilibrium position when a radially outward force against the plurality of longitudinal strips is absent and the distal tip member is longitudinally spaced apart from the plurality of longitudinal strips;

wherein the distal tip member extends proximal of a distal end of the stent and circumferentially surrounds a distal end region of the stent in the delivery configuration.

9. The stent delivery device of claim 8, wherein a proximal portion of the stent is retained in the collapsed configuration by the outer sheath proximal of the radially expanded longitudinal strips.

10. The stent delivery device of claim 8, wherein the stent is biased radially outward against an inner surface of the distal portion of the outer sheath in the delivery configuration.

11. The stent delivery device of claim 8, wherein the plurality of longitudinal strips are self-biased radially inward toward an equilibrium position when a radially outward or radially inward force against the plurality of longitudinal strips is absent.

12. A stent delivery system, comprising:
an outer sheath, wherein the outer sheath comprises a plurality of longitudinal strips extending proximally from the distal end of the outer sheath, wherein an outer surface of the plurality of longitudinal strips defines an outermost surface of the stent delivery system;

an inner shaft slidably disposed within a lumen of the outer sheath;

a self-expanding stent disposed radially between the inner shaft and the outer sheath in a radially collapsed configuration and exerting a radially outward force against an inner surface of the outer sheath; and a distal tip member fixedly attached to a distal end of the inner shaft and moveable between a delivery configuration in which a proximal portion of the distal tip member circumferentially surrounds a distal end of the outer sheath and a deployment configuration in which the distal tip member is positioned distal of the distal end of the outer sheath;

wherein in the deployment configuration, the plurality of longitudinal strips are urged radially outward by the radially outward force of the stent to a radially outward position to permit a distal portion of the stent to radially expand;

wherein the plurality of longitudinal strips are self-biased radially inward to assume an equilibrium position when not subjected to the radially outward force exerted by the stent and the distal tip member is in the deployment configuration, the radially outward position being radially outward of the equilibrium position.

13. The stent delivery system of claim 12, wherein after the distal portion of the stent radially expands, a proximal portion of the stent is retained within the outer sheath proximal of the plurality of longitudinal strips.

14. The stent delivery system of claim 13, wherein after the distal portion of the stent radially expands, proximal retraction of the outer sheath relative to the stent releases the proximal portion of the stent.

15. The stent delivery system of claim 12, wherein in the equilibrium position, the plurality of longitudinal strips do not extend radially outward of an outer surface of the outer sheath proximal of the plurality of longitudinal strips.

16. The stent delivery system of claim 12, wherein in the delivery configuration, the distal tip member extends proximal of a distal end of the stent such that at least a portion of the stent is circumferentially surrounded by the proximal portion of the distal tip member.

17. The stent delivery system of claim 12, wherein the plurality of longitudinal strips are self-biased radially inward to assume an equilibrium position when in the absence of any radially outward or radially inward force against the plurality of longitudinal strips.

* * * * *